United States Patent [19]

Anno

[11] 3,986,956
[45] Oct. 19, 1976

[54] ARTIFICIAL KIDNEY DEVICE
[75] Inventor: Gousuke Anno, Inagi, Japan
[73] Assignee: Tokyo Shibaura Electric Co., Ltd., Kawasaki, Japan
[22] Filed: Dec. 4, 1974
[21] Appl. No.: 529,500

[30] Foreign Application Priority Data
Dec. 4, 1973 Japan.............................. 48-135970

[52] U.S. Cl. ............................ 210/137; 210/321 B
[51] Int. Cl.² ................... B01D 31/00; B01D 13/00
[58] Field of Search...................... 210/137, 321, 22; 251/5; 128/214 F

[56] References Cited
UNITED STATES PATENTS
| | | | |
|---|---|---|---|
| 2,590,215 | 3/1952 | Sausa | 251/5 X |
| 2,766,765 | 10/1956 | Bolanowski et al. | 251/5 X |
| 2,904,063 | 9/1959 | Wall et al. | 251/5 X |
| 3,228,397 | 1/1966 | Moss | 251/5 X |
| R26,006 | 4/1966 | Gewecke | 128/214 F |

Primary Examiner—Frank A. Spear, Jr.
Attorney, Agent, or Firm—Finnegan, Henderson, Farabow & Garrett

[57] ABSTRACT

An artificial kidney device is provided with a dialyzer for separating specified components from blood. A double walled tube is mounted midway of a tube provided for transporting the blood passed through the dialyzer into a vein of a human being, so as to automatically maintain an ultrafiltration pressure substantially constant. The double-tube wall consists of a flexible inner tube and a non-flexible outer tube and is adapted to automatically collapse or inflate the inner tube in response to a change in pressure prevailing within the dialyzer, by applying a predetermined pressure to a closed chamber defined between the inner tube and the outer tube.

14 Claims, 10 Drawing Figures

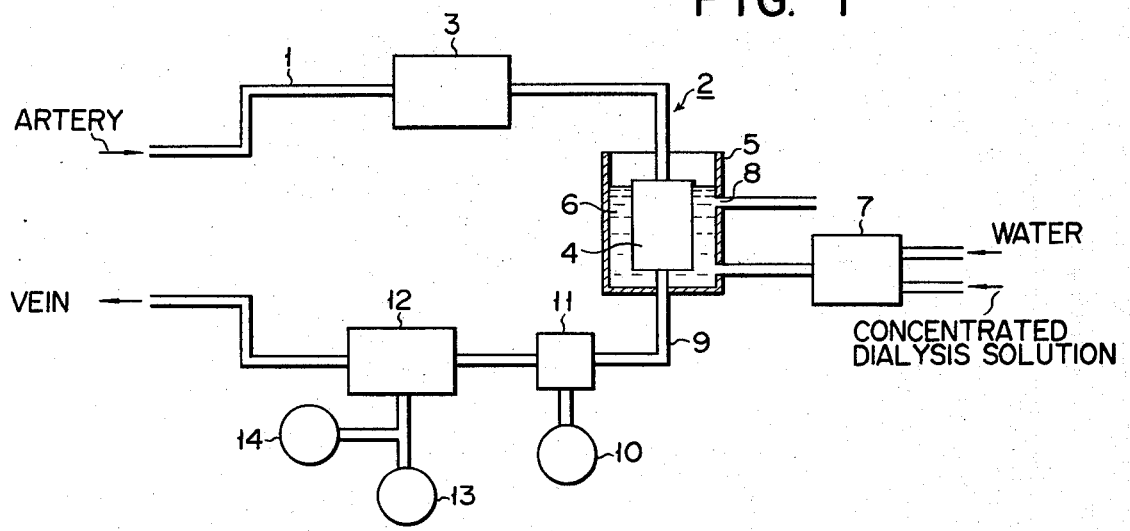
FIG. 1
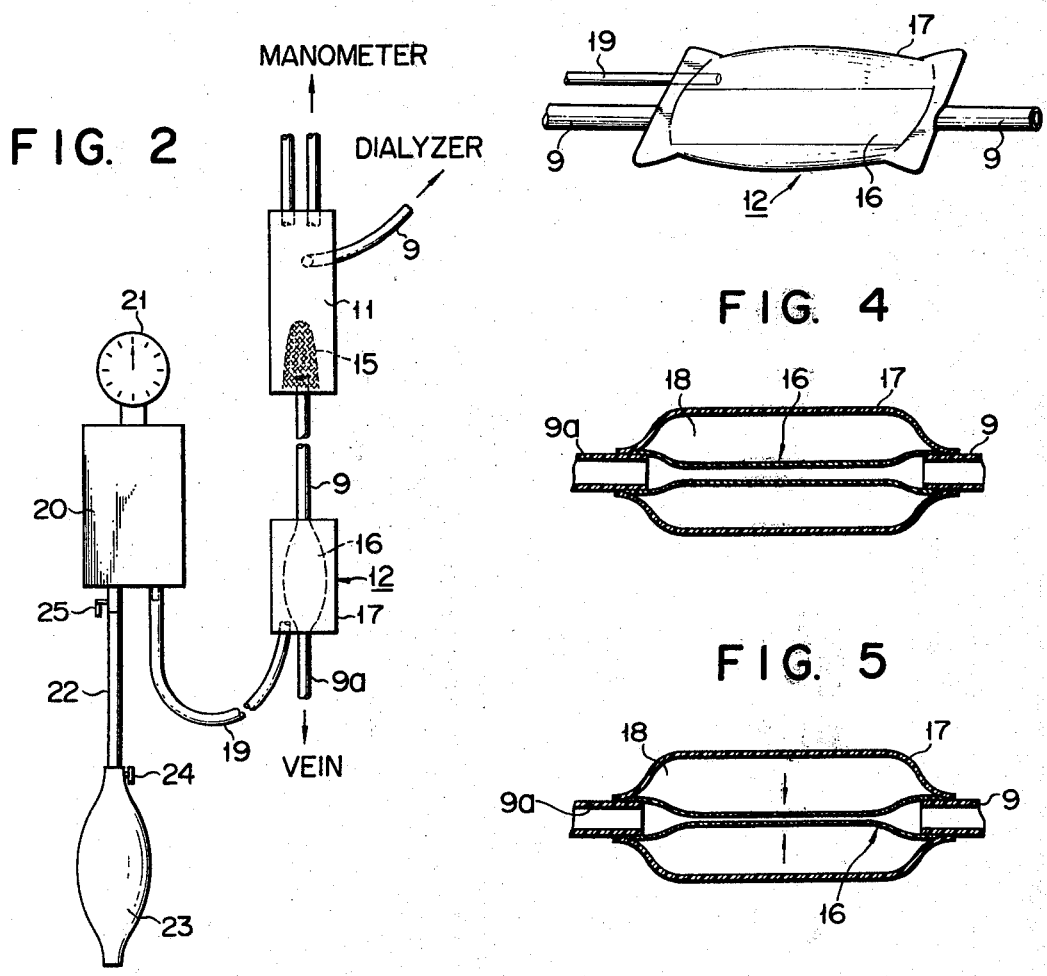

ARTIFICIAL KIDNEY DEVICE

BACKGROUND OF THE INVENTION

This invention relates to an artificial kidney device and in particular an artificial kidney device for automatically maintaining an ultrafiltration pressure substantially constant.

By "an ultrafiltration pressure" is meant a difference between internal and external pressures applied to a dialysis membrane consisting of a semipermeable membrane which is provided within a dialyzer.

A variety of artificial kidney devices, for example, a coil-type one, kiil-type one or one utilizing hollow fibers has been known up to this date. These artificial kidney devices are adapted to send blood from the artery of a human being through a suitable means to a dialyzer where urea, nitrogen, sodium, potassium, water content etc., included in blood are separated through a semipermeable membrane. The blood passed through the dialyzer is returned to the vein of the human being. With the dialyzer, the water content should be eliminated, in an amount far greater than that of the other components, through the semipermeable membrane. In addition to osmotic pressure, therefore, an additional pressure is generally required for the dialysis operation. One method is to apply ultrafiltration pressure to a dialyzer in an attempt to eliminate more water content. Taking the strength etc. of the semipermeable membrane into consideration, the ultrafiltration pressure is generally desired to be maintained at a level of 200 mm Hg. If the ultrafiltration pressure is too high, there is a fear that blood will flow out due to a breakage of the semipermeable membrane. If, on the other hand, it is too low, a dialyzing effect is lowered, and water content is not sufficiently eliminated from blood. For the purpose of maintaining the ultrafiltration pressure at suitable level, a method employed in the prior art is to mount a pinch-cock at a midway of a tube extending from a dialyzer into a vein of a human being. An ultrafiltration pressure of, for example, 200 mm Hg can be provided by restricting the flow passage of the tube by means of the pinch-cock.

However, a very delicate operation of the pinch-cock is required in adjusting the ultrafiltration pressure. Any slight operation of the pinch-cock causes a greater change in the resistance of blood. To make the ultrafiltration pressure at a prescribed level, therefore, the adjustment of the pinch-cock is conducted gradually, i.e., by repeating the adjustment several times. It will take more than 2 minutes for ultrafiltration pressure to settle down to a prescribed level after one adjustment has been made. For this reason, more than 10 minutes will be required in adjusting the ultrafiltration pressure to a desired level. If no due care should be exercised during adjustment, there is a chance that blood will flow out due to a breakage of the dialysis membrane.

The ultrafiltration pressure is related not only to the extent to which the pinch-cock is closed but also to the operation of transporting means of blood from the artery of a human being into a dialyzer, for example, rotations of a pump. If, therefore, the pump is changed in the number of rotations to increase a flow of blood, the above-mentioned delicate adjustment will be required on each occasion.

SUMMARY OF THE INVENTION

It is accordingly the object of this invention to provide an artificial kidney device equipped with a pressure adjusting means capable of automatically maintaining an ultrafiltration pressure of a dialyzer at all times substantially constant irrespective of the variations of blood pressure or a change in the number of rotations of a pump and capable of being manufactured at lower cost without involving any complicated structure.

With an artificial kidney device according to this invention, a double-walled tube is mounted midway of a tube provided for transporting, into a vein of a human being, blood passed through a dialyzer for separating specified components from blood. The double-walled tube consists of a flexible inner tube communicating with said blood-transporting tube and a non-flexible outer tube surrounding the inner tube to define a closed chamber therebetween. The inner tube is automatically collapsed or inflated, in response to a change in an internal pressure prevalent within a dialyzer, due to a difference between an internal pressure of the inner tube and an internal pressure within the closed chamber, whereby an ultrafiltration pressure is automatically maintained substantially constant.

BRIEF DESCRIPTION OF THE DRAWING

This invention will be further described, by way of example, by reference to the accompanying drawings.

FIG. 1 is a schematic general view showing an artificial kidney device according to this invention;

FIG. 2 is a schematic view showing the major part of this invention;

FIG. 3 is an enlarged, perspective view showing a pressure adjusting means comprised of a double-walled tube;

FIGS. 4 and 5 are longitudinal cross-sectional views respectively showing widely open and collapsed states of the pressure adjusting means of FIG. 3;

DETAILED DESCRIPTION OF THE PREFERRED EMBODIMENTS

Figure 8:
FIGS. 8 and 9 are cross-sectional views showing modified forms of an inner tube of the double-walled tube of FIG. 3.

FIG. 1 is a schematic diagram showing an artificial kidney device according to this invention which is provided with a coil type dialyzer. A tube 1 is connected at one end to the artery of a human being and at the other end to the dialyzer 2. Midway of the tube 1 is connected a pump 3 for sending blood to the dialyzer 2 at a predetermined flow rate. The dialyzer 2 is a known coil-type one formed by winding one or a plurality of semipermeable membranes, into a coil 4 with a mesh interposed therebetween and submerging the coil into a dialysis solution within a container 5. The dialysis solution is one having a specified concentration which is prepared by mixing at a mixer 7 and at a suitable ratio, water and an undiluted solution containing, for example, sodium chloride etc. The dialysis solution from the mixer 7 is sequentially forwarded to and discharged from an outlet 8 while it is contacted with a dialysis membrane. On the other hand, blood is passed through the dialyzer 2, where unnecessary components are separated, and flows through a tube 9 into the vein of the human being. Midway of the tube 9, a drip tube 11 connected to a manometer 10 and a double-walled tube 12 are provided in communication with the tube 9. An air pump 13 and air reservoir 14 communicate with the double-walled tube. FIGS. 2 to 9 show the detail of the double-walled tube and its modifications. As shown in FIG. 2 the blood passed through the dialyzer 2 is sent through the tube 9 to the drip tube 11. Since the manometer 10 is connected to the drip tube 11, a pressure prevailing within the drip tube 11, or consequently an ultrafiltration pressure prevailing at the dialyzer 2, is indicated at the manometer 10. 15 denotes a mesh. The drip tube 11 etc. are conventionally known and may be suitably selected by those skilled in the art.

Figure 6:
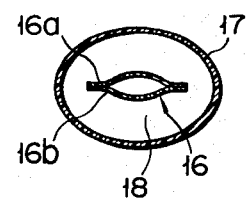
FIGS. 6 and 7 are cross-sectional views showing the pressure adjusting means of FIG. 3, each corresponding to FIG. 4 and FIG. 5.

The blood passed through the drip tube flows into the double-walled tube 12. The double-walled tube 12 has an inner tube 16 as shown in FIGS. 3 to 7 and an outer tube 17. The inner tube 16 is made of, for example, non-rigid polyvinyl chloride and has such a relatively thin wall that it can be easily collapsed. As shown in FIGS. 4 and 6, the inner tube 16 is formed by superposing one over the other two sheets of non-rigid polyvinyl chloride wider than the diameter of the tube 9 and sealing them at the side edge portions. The outer tube 17 is formed to have such a rigidity that it is not deformed under the maximum pressure to be applied in use. It is made of, for example, a rigid polyvinyl chloride and has a form substantially elliptical in cross section. The inner and outer tubes 16 and 17 of the double-walled tube 12 are hermetically heat sealed at each end to define a closed chamber 18 between the inner and outer tubes 16 and 17. The tube 19 opened at one end into the closed chamber 18 and at the other end detachably connected to an air reservoir 20. The air reservoir is made, for example, of acrylic acid resin and has a cylindrical shape. A manometer 21 is connected to the air reservoir 20, indicating an air pressure within the air reservoir 20. A manually operated air pump 23 consisting of a rubber bulb is connected through a tube 22 to the air reservoir 20 and adopted to adjust the air pressure prevailing within the closed chamber 18. 24 denotes a valve for releasing the air confined within the air reservoir 20. 25 denotes a valve for controlling a flow of the air reservoir 20.

An explanation will now be made as to how an ultrafiltration pressure is automatically controlled in the so constructed artificial kidney.

Blood from the artery of a human being is sent to the dialyzer 2 while being gradually increased in amount by changing the number of rotations of the pump 3. The air pump 23 is repeatedly squeezed by the hand of an operator so that a pressure prevailing within the dialysis coil of the dialyzer 2 comes to, for example, 200 mm Hg. When the manometer 10 connected to the drip tube 11 indicates just 200 mm Hg, the squeezing operation of the pump 23 is stopped and the valve 25 is closed. Since, at this time, the weight of blood occupied from the drip tube 11 down to the double-walled tube 12 is applied, air pressures within the closed chamber 18 and air reservoir 20 are increased by that extent and maintained at levels somewhat higher than 200 mm Hg.

The establishment of the ultrafiltration pressure may be conveniently conducted preliminarily setting a pressure within the closed chamber 18 by watching the manometer 21 at a value little higher than that of the ultrafiltration pressure. But the manometer 21 may be omitted.

Figure 7:
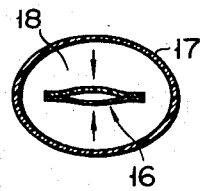

When the pressure within the dialysis coil 4 is maintained to 200 mm Hg, blood is sent toward the vein side in a manner that the double-walled tube 12 is inflated to suitable extent shown, for example, in FIGS. 4 and 6. When, however, the pressure within the dialysis coil 4 comes to below 200 mm Hg, the inner tube 16 of the double-walled tube 12 is collapsed as shown in FIGS. 5 and 7 with its cross-sectional opening being narrowed, since the internal pressure of the inner tube 16 is smaller than the external pressure of the inner tube 16. In this case, the inner tube 16 is closed in a direction indicated by arrows in FIG. 5, because the inner tube 16 tends to be more easily collapsed in a vertical i.e., than in a horizontal direction. As the inner tube 16 is so collapsed, the blood passed through the dialysis coil is restricted, causing the ultrafiltration pressure i.e., the pressure prevailing within the dialysis coil 4 to be increased. As a result, the ultrafiltration pressure is automatically adjusted to 200 mm Hg. When, on the other hand, the pressure within the dialysis coil 4 exceeds 200 mm Hg, the internal pressure of the inner tube 16 exceeds the external pressure of the inner tube 16, causing the inner tube 16 to be again inflated as shown in FIG. 4. As a result, blood flow rate is increased and the pressure prevailing within the dialysis coil is dropped and automatically adjusted to 200 mm Hg. In this way, the ultrafiltration pressure i.e. the pressure within the dialysis coil is automatically maintained to 200 mm Hg. This automatic adjustment is effected within several seconds to scores of seconds. Though a volume within the closed chamber 18 is somewhat changed due to the collapse or inflation of the inner tube 16, this change is absorbed by a relatively great amount of air confined within the air reservoir 20. Consequently, the change of pressure within the closed chamber 18 due to the collapse or inflation of the inner tube 16 can be disregarded. The change of pressure within the inner tube 16 due to the collapse or inflation of the inner tube 16 is decreased as the volume of the air reservoir 20 is increased. From this viewpoint the greater the volume of the air reservoir 20, the better. There is, however, a fear that if by any chance the inner tube 16 should be ruptured, a greater amount of air flows into the blood vessel of the human being. If, on the other hand, the volume of the air reservoir 20 is too small, the change of pressure within the closed chamber 18 due to the collapse or inflation of the inner tube 16 can not be disregarded. Taking into consideration the safety of the inner tube 16 against rupture as well as the necessity to absorb the change of pressure resulting from the inflation or constriction of the inner tube 16, it is preferred that the volume of the air reservoir be of the order of about 70 ml. If the closed chamber 18 is designed to have an ample volume, the air reservoir can be omitted. In this case, however, the cost of the double-walled tube is raised.

Figure 10:
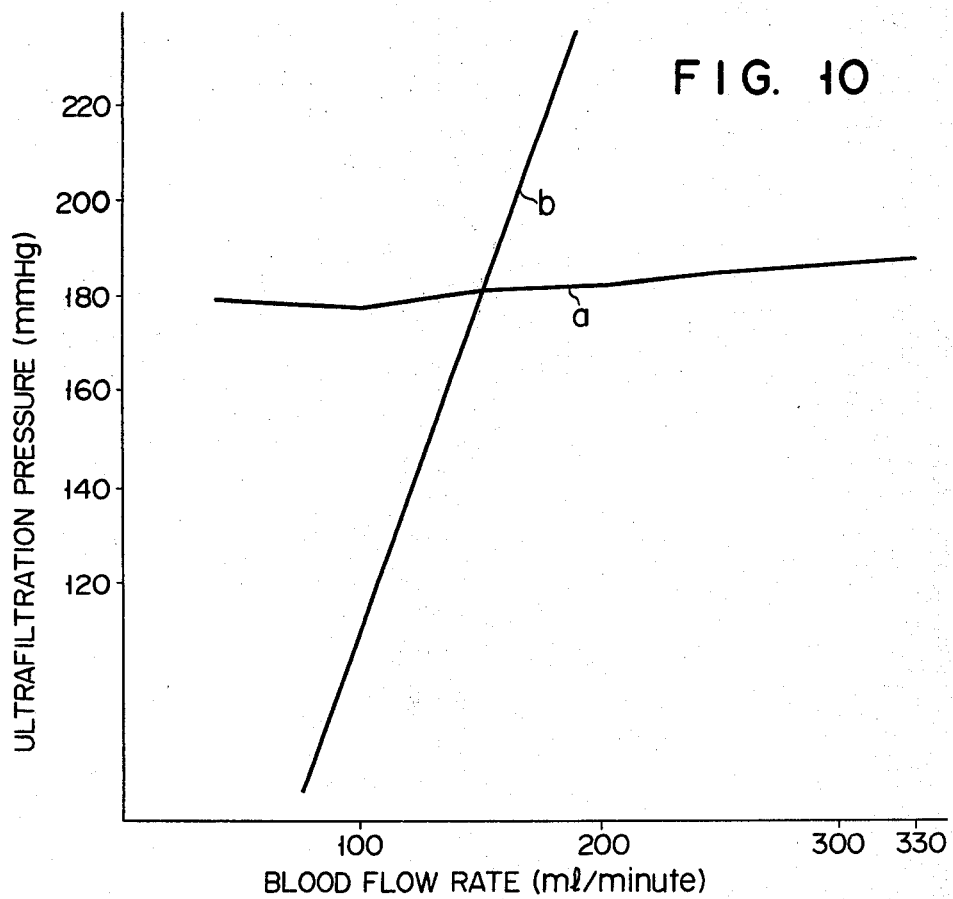
FIG. 10 is a graph showing a comparison in ultrafiltration pressure holding characteristic between the artificial kidney device according to this invention and the prior art artificial kidney device.

FIG. 10 is a graph showing the result of measurement made as to the effect, on the ultrafiltration pressure, of a change in the flow of blood from the artery of a human being. For comparison, measurement was also made of the case where a conventional pinch-cock is used. A curve $a$ appearing in the graph of FIG. 10 shows a change in the ultrafiltration pressure of the artificial kidney device according to this invention as obtained when a flow of blood is changed in a range of 50 cc/minute to 330 cc/minute by changing the number of rotations of the pump 3, wherein the ultrafiltration pressure is at first set at 180 mm Hg when the flow of blood is 150 ml/minute. On the other hand, a curve b appearing in the graph of FIG. 10 shows the change of ultrafiltration pressure when a flow of blood is changed by changing the number of rotations of the pump 3, wherein the ultrafiltration pressure is at first set at 180 mm Hg when the flow of blood is 150 ml/minute and that the conventional pinch-cock is used. From the curve a it will be seen that according to this invention the ultrafiltration pressure is maintained substantially constant, even if the flow rate of blood is widely changed. In the case of the curve b, on the other hand, it will be easily understood that a slight change in the flow rate of blood will cause a large or great change in the ultrafiltration pressure. The ultrafiltration pressure is, therefore, very unstable.

According to this invention, once a predetermined pressure is applied to the closed chamber 18 of the double-walled tube 12, the ultrafiltration pressure is maintained substantially constant even in the event of any change in the number of rotations of the pump 3. This obviates the necessity of making a troublesome and time-consuming adjustment. Furthermore, there is less chance that a dialysis membrane will be ruptured due to a pressure prevalent within the dialysis coil being excessively raised under no due care or attention. In the operation of the prior art artificial kidney device wherein a pinch-cock is employed as described above, it is necessary for the attendant to pay, at all times, due care or attention to the ultrafiltration pressure. According to this invention, only an occasional check on the ultrafiltration pressure is required. Consequently, a fatigue on the part of the attendant can be prominently alleviated. Where a medical treatment is effected at night, a safety as well as a labor-saving is required. This invention will prove advantageous even in such cases.

According to this invention the ultrafiltration pressure can be maintained substantially constant by a combination, with a pressure applying mechanism, of the double-walled tube 12 consisting of the inner tube 16 and the outer tube 17. This makes the device simple in construction and low in manufacturing cost. After use, the double-walled tube can be detached from the pressure mechanism for disposal.

Figure 9:

Though with the above-mentioned embodiment the inner tube 16 of the double-walled tube 12 is formed by heat sealing the pair of sheets at their side edge portions, it may take a variety of forms if it is easily collapsible. For example, it may take a form 26 elliptical in cross section as shown in FIG. 8 or a flattened tubular form 27 as shown in FIG. 9, or it may be formed by folding back a sheet upon itself and sealing the opposite free side edge portions thereof. As a material for the inner tube 15, use is made of, in addition to the above-mentioned polyvinyl chloride, the other flexible synthetic resins, rubbers or flexible air-impermeable sheets. It is, however, required that these materials can be easily deformed in response to a difference between the internal and external pressures of the inner tube 16 and that they are harmless to blood or a human being. For the outer tube 17, any material may be used as far as it is not deformed under any available pressure applied to the closed chamber 18. However, a rigid thermoplastic synthetic resin is considered preferable from the standpoint of the easiness in manufacture etc.

Though with the above-mentioned embodiment the air pressure is applied to the closed chamber, any fluid pressure may be applied to the closed chamber. Use of water, however, assures a safety against the possible rupture of the inner tube 16.

The artificial kidney device according to this invention may be applied not only to the above-mentioned coil type dialyzer, but also to all dialyzers including one using hollow fibers which are adapted to effect dialysis utilizing an ultrafiltration pressure.

What is claimed is:

1. An artificial kidney device for a human being comprising:
   a dialyzer for removing specified components from blood;
   blood pumping means for transporting blood from an artery of the human being to the dialyzer and creating a blood pressure in the dialyzer above arterial pressure;
   means forming a flow passage in communication with said dialyzer for transporting blood passed through the dialyzer to a vein of the human being;
   means for maintaining a substantially constant ultrafiltration pressure in said dialyzer including an inner tube forming part of said flow passage and an outer tube surrounding said inner tube and defining a closed chamber therewith, the pressure within said inner tube being subject to change in accordance with prevailing blood pressure in said dialyzer; and
   means for applying and maintaining a substantially constant predetermined pressure in excess of atmospheric pressure within said closed chamber;
   said inner tube being formed of material deformable in response to changes in pressure within said inner tube and the pressure differentials created thereby between the inside of said inner tube and said chamber to enlarge or restrict said flow passage through said inner tube so that the pressure inside said inner tube will balance the substantially constant predetermined pressure in said closed chamber to thereby maintain said ultrafiltration pressure in the dialyzer substantially constant.

2. An artificial kidney device according to claim 1, wherein said inner tube is formed of unrigid polyvinyl chloride.

3. An artificial kidney device according to claim 1 wherein said outer tube is formed of a material substantially nondeformable under the pressure applied to said chamber by said pressure applying and maintaining means.

4. An artificial kidney device according to claim 3, in which said inner tube is made of a flexible material and has a flattened tubular configuration, and said outer tube is formed of inflexible material.

5. An artificial kidney device according to claim 3, wherein said outer tube is formed of rigid polyvinyl chloride.

6. An artificial kidney device according to claim 3, wherein said inner tube is formed of relatively thin plastic material, and said outer tube is formed of relatively thick plastic material.

7. An artificial kidney device according to claim 3 wherein said inner and outer tubes comprise a double walled tube, said transport means including a tube, said inner and outer tubes being heat-sealed in airtight relation to said transport tube.

8. An artificial kidney according to claim 3 wherein said inner tube is formed of a deformable flexible material which is non-self-recoverable upon deformation.

9. An artificial kidney device according to claim 1 wherein said inner tube comprises a pair of flexible sheets sealed one to the other along side edge portions thereof.

10. An artificial kidney device according to claim 1 including an air reservoir connected to said outer tube in communication with said closed chamber.

11. An artificial kidney device according to claim 10 wherein said air reservoir has a volume of sufficient capacity in relation to the capacity of said chamber such that the deformation of said inner tube causes an insignificant pressure change within said chamber.

12. An artificial kidney device according to claim 11 wherein said air reservoir has a volume of about 70 ml.

13. An artificial kidney device according to claim 1 wherein said pressure applying means for said chamber comprises a hand-operated air pump including an elastic bulb.

14. An artificial kidney device according to claim 1 including means carried by the first mentioned maintaining means for substantially eliminating pressure changes in said chamber caused by deformation of said inner tube.

* * * * *